(12) United States Patent
Otsubo et al.

(10) Patent No.: US 7,449,015 B2
(45) Date of Patent: Nov. 11, 2008

(54) PANTS-TYPE DISPOSABLE WEARING ARTICLE

(75) Inventors: Toshifumi Otsubo, Kagawa-ken (JP); Shunsuke Takino, Kagawa-ken (JP)

(73) Assignee: Uni-Charm Co., Ltd., Ehime, ken (JP)

( * ) Notice: Subject to any disclaimer, the term of this patent is extended or adjusted under 35 U.S.C. 154(b) by 359 days.

(21) Appl. No.: 10/839,708

(22) Filed: May 6, 2004

(65) Prior Publication Data
US 2005/0010186 A1    Jan. 13, 2005

Related U.S. Application Data

(63) Continuation of application No. PCT/JP03/00915, filed on Jan. 30, 2003.

(30) Foreign Application Priority Data

Jan. 30, 2002  (JP) ............... 2002-020804
Jan. 28, 2003  (JP) ............... 2003-018205

(51) Int. Cl.
*A61F 13/15* (2006.01)

(52) U.S. Cl. ............... 604/385.26; 604/385.24; 604/385.25; 604/385.29; 604/385.27

(58) Field of Classification Search ............ 604/385.24, 604/385.25, 385.29, 385.27, 396, 389, 385.01, 604/385.26

See application file for complete search history.

(56) References Cited

U.S. PATENT DOCUMENTS 5,447,508 A * 9/1995 Numano et al. ......... 604/385.27

6,482,195 B1 * 11/2002 Kumasaka ............. 604/385.27

FOREIGN PATENT DOCUMENTS

| EP | 0 761 194 | 3/1997 |
|---|---|---|
| EP | 0 990 434 | 4/2000 |
| EP | 1 212 999 | 6/2002 |
| JP | 3-122824 | 12/1991 |
| JP | 08-112309 | 5/1996 |
| JP | 11-036103 | 2/1999 |
| WO | 96/11657 | 4/1996 |

* cited by examiner

*Primary Examiner*—Jacqueline F. Stephens
(74) *Attorney, Agent, or Firm*—Lowe, Hauptman, Ham & Berner LLP

(57) ABSTRACT

A pants-type disposable wearing article includes leg-circumferential first elastic members attached to crotch region's lateral margins of an outer sheet and waist-circumferential second elastic members attached to waist regions' upper margins of the outer sheet. The elastic members are joined to the sheet while the sheet and the second elastic members are stretched at given extension ratios, respectively, in a transverse direction and the first elastic members is stretched at a given extension ratio in the leg-circumferential direction so that the sheet and the first elastic members may have substantially the same leg-circumferential dimensions after these sheet and first elastic members have been relaxed and the sheet and the second elastic members may have substantially the same transverse dimensions after these sheet and second elastic members have been relaxed. In addition, the waist regions' upper margins and the crotch region's lateral margins are substantially planar.

16 Claims, 8 Drawing Sheets

PANTS-TYPE DISPOSABLE WEARING ARTICLE

This application is a continuation of International Application No. PCT/JP03/000915 filed Jan. 30, 2003, which claims priority to Japanese Application Nos. 2002-020804 filed Jan. 30, 2002 and 2003-018205 filed Jan. 28, 2003, all of which are hereby incorporated by reference herein in their entirety.

BACKGROUND OF THE INVENTION

This invention relates to a pants-type disposable wearing article for absorption and containment of bodily discharges.

Conventional pants-type disposable wearing articles, for example, an article disclosed in Japanese Utility Model Unexamined Publication No. 1991-122824A comprise an elastically stretchable liquid-pervious topsheet lying on a body facing side, a liquid-impervious backsheet lying on an undergarment facing side and a liquid-absorbent core interposed between these top- and backsheets so as to define front and rear waist regions opposed to each other, a crotch region extending between the front and rear waist regions, a waist-opening and a pair of leg-openings.

The aforesaid article has waist regions' upper margins extending across the front and rear waist regions in a transverse direction, waist regions' lateral margins extending in a longitudinal direction and crotch region's lateral margins extending in a leg-circumferential direction. In this article, the waist regions' lateral margins are put flat and joined together in the vicinity of the outermost edges of these lateral margins by means of a plurality of welding lines arranged intermittently in the longitudinal direction. A plurality of elastic members extending in the transverse direction are contractibly attached to the respective waist regions' upper margins. Similarly, a plurality of elastic members extending in the leg-circumferential direction are contractibly attached to the crotch region's lateral margins. The elastically stretchable top- and backsheets cooperate with the waist-circumferential elastic members to tighten the wearer's waist while the top- and backsheets cooperate with the leg-circumferential elastic members to tighten the wearer's legs so as to eliminate a possibility that the article might unintentionally slip down along the wearer's waist and bodily discharges might leak out beyond the crotch region's lateral margins.

In the case of the aforesaid article, the waist regions' upper margins are formed with a plurality of irregular wrinkles or gathers undulating in a thickness direction of the top- and backsheets due to contraction of the waist-circumferential elastic members in the transverse direction. Similarly, the crotch region's lateral margins are formed with a plurality of irregular wrinkles or gathers undulating in the thickness direction of the top- and backsheets due to contraction of the leg-circumferential elastic members in the leg-circumferential direction. Formation of such wrinkles or gathers along the waist regions' upper margins and the crotch region's lateral margins necessarily results in gaps between the wearer's body and the waist regions' upper margins and between the wearer's body and the crotch region's lateral margins. Consequently, bodily discharges might leak out beyond the waist regions' upper margins and the crotch region's lateral margins through those gaps even if the elastic members adequately tighten the wearer's waist and legs. Furthermore, the wrinkles or gathers formed along the waist regions' upper margins and the crotch region's lateral margins may give the wearer more or less uncomfortable feeling and sometimes mark compression traces on the wearer's body.

SUMMARY OF THE INVENTION

In view of the problems described above, it is an object of this invention to provide a pants-type disposable wearing article improved so that both the waist regions' upper margins and the crotch region's lateral margins are free from formation of a plurality of irregular wrinkles or gathers even after the elastic members attached to these margins have been relaxed and neither leakage of bodily discharges beyond the waist regions' margins and the crotch region's lateral margins nor uncomfortable feeling experienced by the article wearer is concerned.

The object set forth above is achieved, according to this invention, by a pants-type disposable wearing article comprising an elastically stretchable outer sheet defining front and rear waist regions opposed to each other and a crotch region extending between these waist regions, and a liquid-absorbent panel attached to an inner surface of the outer sheet and extending between the front and rear waist regions, the outer sheet having waist regions' upper margins extending in the front and rear waist regions in a transverse direction, waist-circumferential lateral margins extending in a longitudinal direction and crotch region's lateral margins extending in the crotch region in the leg-circumferential direction, the front and rear waist regions being connected along the waist-circumferential margins so as to define a waist-opening and a pair of leg-openings, and first elastic members extending in the leg-circumferential direction are attached to the crotch region's lateral margins of the outer sheet.

The outer sheet and the first elastic members are joined together while the outer sheet is stretched at an appropriate given stretching ratio in the transverse direction and the first elastic members are stretched at an appropriate given stretching ratio in the leg-circumferential direction so as to ensure that the outer sheet and the first elastic members have substantially the same dimensions as measured in the leg-circumferential direction after these outer sheet and first elastic members have been relaxed and that the crotch region s lateral margins are substantially planar without undulation in a thickness direction of the outer sheet.

This invention includes the following embodiments.

Waist-circumferential second elastic members extending in the transverse direction are attached to the waist regions' upper margins of the outer sheet and the outer sheet and the second elastic members are bonded together while the outer sheet is stretched at an appropriate given stretching ratio and the second elastic members are stretched at an appropriate stretching ratio both in the transverse direction so as to ensure that the outer sheet and the second elastic members have substantially the same dimensions as measured in the transverse direction after these outer sheet and second elastic members have been relaxed and that the waist regions' upper margins are substantially planar without undulation in a thickness direction of the outer sheet.

A transverse stretch stress in the waist regions' upper margins of the outer sheet is higher than a leg-circumferential stretch stress in the crotch region's lateral margins of the outer sheet and also than a transverse stretch stress in a portion of the outer sheet except the waist regions' upper margins and the crotch region's lateral margins.

The leg-circumferential stretch stress in the crotch region's lateral margins in the outer sheet is higher than the transverse stretch stress in the portion of the outer sheet except the waist regions' upper margins and the crotch region's lateral margins.

The outer sheet is formed by a composite nonwoven fabric layer composed of two elastically stretchable hydrophobic fibrous nonwoven fabric layers placed upon each other and the first and second elastic members are interposed between these nonwoven fabric layers.

The outer sheet is formed by a composite sheet composed of an elastically stretchable hydrophobic fibrous nonwoven fabric layer and a breathable liquid-impervious plastic film joined together and the first and second elastic members are interposed between the nonwoven fabric layer and the film.

The panel comprises a liquid-pervious topsheet lying on a body facing side, a liquid-impervious backsheet lying on an undergarment facing side and a liquid-absorbent core interposed between the top- and backsheets.

DETAILED DESCRIPTION OF THE PREFERRED EMBODIMENTS

Details of a pants-type disposable wearing article according to this invention will be more fully understood from the description given hereunder in reference with the accompanying drawings.

Figure 1:
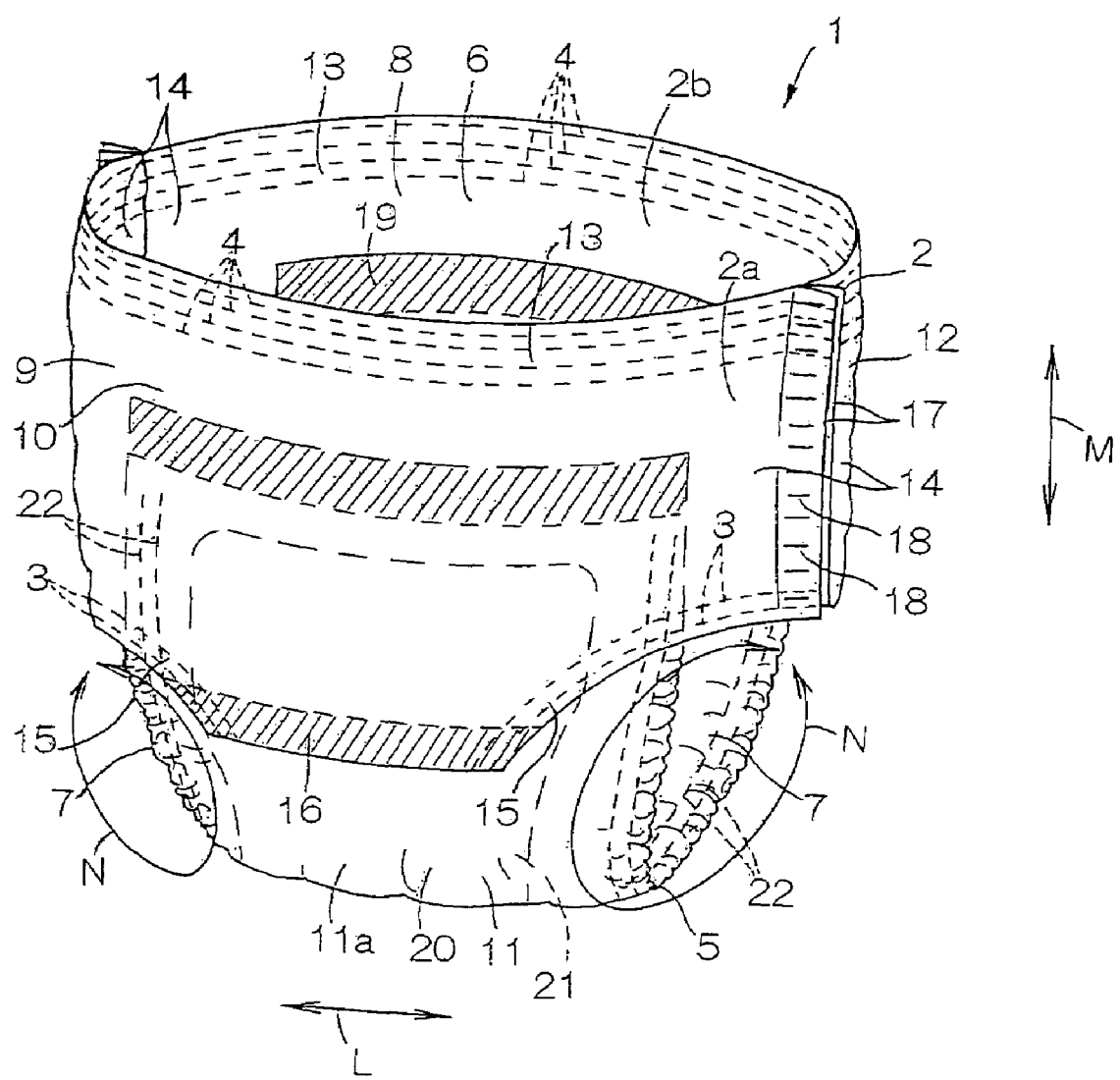
FIG. 1 is a partially cutaway perspective view depicting a wearing article as one embodiment of this invention.
Figure 2:
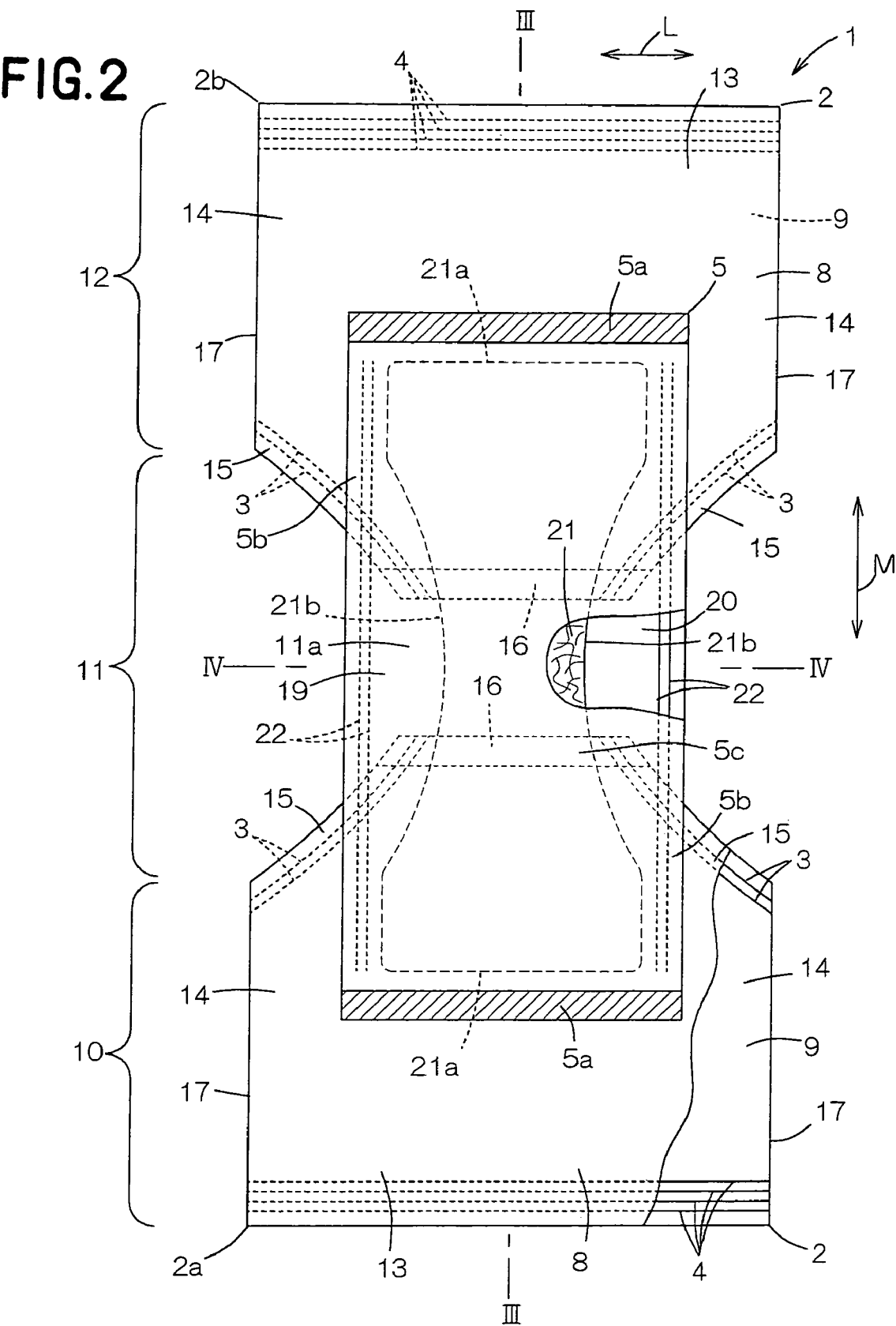
FIG. 2 is a developed plan view depicting the article of FIG. 1 in the state before front and rear waist regions are connected to each other along transversely opposite lateral margins of these waist regions.
Figure 3:
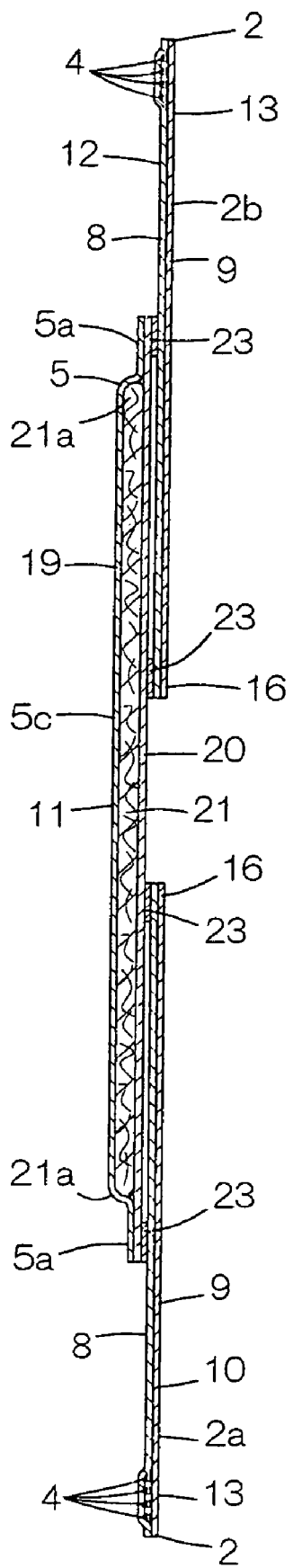
FIG. 3 is a sectional view taken along a line III-III in FIG. 2.
Figure 4:
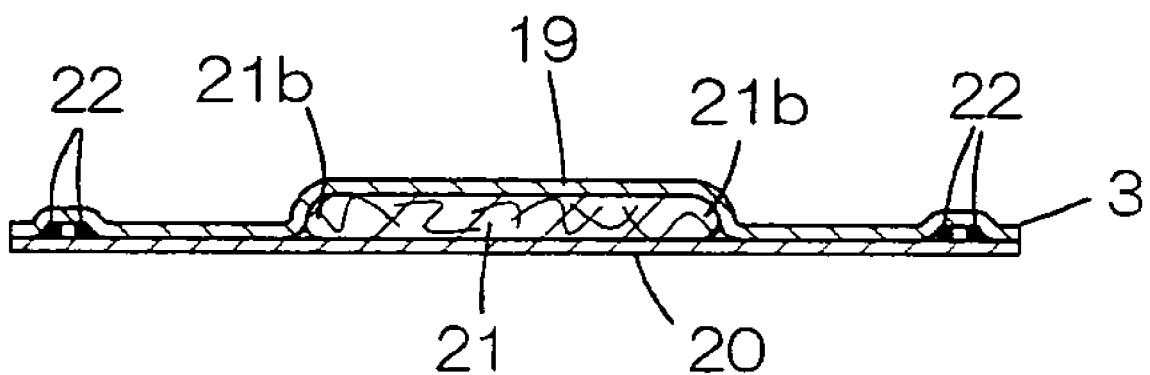
FIG. 4 is a sectional view taken along a line IV-IV in FIG. 2.

FIG. 1 is a perspective view of an wearing article 1 illustrated as one embodiment of this invention, FIG. 2 is a partially cutaway plan view depicting this article 1 in its state prior to connection of front and rear waist regions to each other along transversely opposite waist regions' lateral margins, and FIGS. 3 and 4 are sectional views taken along lines III-III and IV-IV in FIG. 2, respectively. In FIGS. 1 and 2, a transverse direction is indicated by an arrow L, a longitudinal direction is indicated by an arrow M and a leg-circumferential direction is indicated by an arrow N (only in FIG. 1). Expression "inner surfaces" of an outer sheet 2 and top- and backsheets 19, 20 should be understood to be the surfaces thereof facing a core 21 and expression "outer surfaces" of these sheets 2, 19, 20 should be understood to be the surfaces thereof facing away from the core 21.

The article 1 comprises the elastically stretchable and liquid-impervious outer sheet 2, first elastic members 3 extending in the leg-circumferential direction and second elastic members 4 extending in the waist-circumferential direction both attached to the outer sheet 2, and a liquid-absorbent panel 5 attached to the inner surface of the outer sheet 2. The article 1 is of pants-type having a waist-opening 6 and a pair of leg-openings 7 lying below the waist-opening 6.

The outer sheet 2 is formed by a composite nonwoven fabric comprising two layers 8, 9 of elastically stretchable hydrophobic fibrous nonwoven fabric placed upon each other and elastically stretchable in the longitudinal and transverse directions as well as in the leg-circumferential direction. The nonwoven fabric layers 8, 9 have respective surfaces opposed and intermittently bonded to each other by means of adhesive (not shown). The outer sheet 2 defines a front waist region 10 and a rear waist region 12 opposed to each other and a crotch region 11 extending between these waist regions 10, 12. The outer sheet 2 is divided into a first outer sheet section 2a lying on the side of the front waist region 10 and a second outer sheet section 2b lying on the side of the rear waist region 12.

The outer sheet 2 has waist regions' upper margins 13 lying outside longitudinally opposite ends 5a of the panel 5 so as to extend across the front and rear waist regions 10, 12 in the transverse direction, waist regions' lateral margins 14 lying outside transversely opposite side edges 5b of the panel 5 in the front and rear waist regions 10, 12 so as to extend in the longitudinal direction, crotch region's lateral margins 15 lying outside the transversely opposite side edges 5b in the crotch region 11 so as to extend in the leg-circumferential direction, and lower margins 16 lying in the crotch region 11 so as to extend across the panel 5.

As will be seen in FIG. 2, the crotch region's lateral margins 15 destined to define peripheries of the respective leg-openings 7 curve inward as viewed in the transverse direction of the article 1 as these crotch region's lateral margins 15 get nearer to a longitudinally middle zone 11a of the crotch region 11. In other words, a transverse dimension of the lower margin 16 is smaller than that of the upper margin 13. These two lower margins 16 opposed to each other in the longitudinally middle zone 11a of the crotch region 11 are spaced from each other by a given dimension. In the outer sheet 2, The respective sheet sections 2a, 2b are put flat together along the waist regions' lateral margins 14 thereof and joined together in the vicinity of side edges 17 of these waist regions lateral margins 14 by means of a plurality of welding lines 18 arranged intermittently in the longitudinal direction.

It is not essential to divide the outer sheet 2 into the first and second outer sheet sections 2a, 2b but the lower margins 16 of these sheet sections 2a, 2b may be contiguous to each other in the crotch region 11 so as to define the whole area of the crotch region 11. In this case, the outer sheet 2 has the waist regions' upper margins 13 and the waist regions' lateral margins 14 extending in the front and rear waist regions 10, 12 and the crotch region's lateral margins 15 extending in the crotch region 11.

The first elastic members 3 associated with the respective leg-openings are arranged along the crotch region s lateral margins 15 of the crotch region so as to extend in the leg-circumferential direction. The first elastic members 3 comprise a plurality of elastic threads spaced one from another by a given dimension in the transverse direction. The second elastic members 4 associated with the waist-opening are arranged along the waist regions' upper margins 13 so as to extend in the transverse direction. The first elastic members 3 and the second elastic members 4 are interposed between the nonwoven fabric layers 8, 9 constituting the outer sheet 2 and secured to the respective surfaces of these nonwoven fabric layers 8, 9 opposed to each other by means of adhesive (not shown) It should be understood that the desired effect can be achieved by securing these elastic members 3, 4 to the nonwoven fabric layers 8, 9 only along the waist regions' lateral margins 14 and the respective lower margins 16 of the outer sheet sections. In other words, it is not essential to secure these elastic members 3, 4 to the nonwoven fabric layers 8, 9 in a regions defined between those lateral margins 14 and lower margins 16.

The outer sheet 2 and the first elastic members 3 are joined together while the sheet 2 is stretched at a given stretching ratio in the transverse direction and the first elastic members 3 are stretched at a given stretching ratio in the leg-circumferential direction. After the sheet 2 and the first elastic members 3 have been joined together in this manner, such stretching force is released and both the outer sheet 2 and the first elastic members 3 are allowed to contract. After the stretching force has been released, the outer sheet 2 and the first elastic members 3 restore respective initial leg-circumferential dimensions which are substantially equal one to another. Consequently, there is no possibility that the crotch region's lateral margins 15 of the outer sheet 2 might be formed with a plurality of irregular wrinkles or gathers due to the contraction of the first elastic members 3. In addition, there is no possibility that the crotch region's lateral margins 15 of the outer sheet 2 might undulate in a thickness direction of the sheet 2, so these lateral zones 15 destined to define the peripheries of the leg-openings are substantially planar.

The outer sheet 2 has a predetermined residual strain causing a dimensional difference (i.e., hysteresis error) between dimension of the outer sheet 2 before it is stretched and the dimension thereof after it was stretched and then allowed to contract. Similarly, the first elastic members 3 have a predetermined residual strain causing a dimensional difference (i.e., hysteresis error) between the dimension of the first elastic members 3 before these members 3 are stretched and the dimension thereof after these members 3 have been stretched and then allowed to contract. In general, the residual strain exhibited by the outer sheet 2 is more or less different from the residual strain exhibited by the first elastic members 3 because the residual strain depends on various factors such as quality of material, length, width and thickness.

It is assumed that the outer sheet 2 and the first elastic members 3 respectively exhibiting different residual strains are joined together while these outer sheet 2 and elastic members 3 are stretched at one and same stretching ratio and then allowed to contract. In this case, a differential residual strain between these outer sheet 2 and elastic members 3 will inevitably result in a dimensional difference between these outer sheet 2 and elastic members 3 after they have been allowed to contract. Eventually, the circumferential lateral margins 15 of the waist regions will be formed with wrinkles or gathers. To overcome this problem, respective stretching ratios of the outer sheet 2 and the first elastic members 3 are preadjusted in the article 1 according to this invention by taking account of the residual strains peculiar to the outer sheet 2 and the first elastic members 3 so that the outer sheet 2 and the first elastic members 3 may have substantially the same dimensions in the leg-circumferential direction. In this way, there is no anxiety that any significant wrinkles or gathers might appear along the crotch region's lateral margins 15 destined to define the peripheries of the respective leg-openings even after the outer sheet 2 and the first elastic members 3 have contracted.

The outer sheet 2 and the second elastic members 4 are joined together while the sheet 2 is stretched at a given stretching ratio in the transverse direction and the second elastic members 4 are stretched at a given stretching ratio in the transverse direction. After the sheet 2 and the second elastic members 4 have been joined together in this manner, such stretching force is released and both the outer sheet 2 and the second elastic members 4 are allowed to contract. After the stretching force has been released, the outer sheet 2 and the second elastic members 4 restore respective initial transverse dimensions which are substantially equal one to another. Consequently, there is no possibility that the waist regions' lateral margins 13 of the outer sheet 2 might be formed with a plurality of irregular wrinkles or gathers due to the contraction of the second elastic members 4. In addition, there is no possibility that the waist regions' lateral margins 13 of the outer sheet 2 might undulate in a thickness direction of the sheet 2, so these lateral zones 13 destined to define the peripheries of the waist-opening are substantially planar.

The second elastic members 4 have a predetermined residual strain causing a dimensional difference (i.e., hysteresis error) between the dimension of the second elastic members 4 before these members 4 are stretched and the dimension thereof after these members 4 have been stretched and then allowed to contract. As has been described just above, the residual strain exhibited by the outer sheet 2 is more or less different from the residual strain exhibited by the second elastic members 4 because the residual strain depends on various factors such as quality of material, length, width and thickness.

Now it is assumed that the outer sheet 2 and the second elastic members 4 respectively exhibiting different residual strains are joined together while these outer sheet 2 and elastic members 4 are stretched at one and same stretching ratio and then allowed to contract. In this case, a differential residual strain between these outer sheet 2 and elastic members 4 will inevitably result in a dimensional difference between these outer sheet 2 and elastic members 4 after they have been allowed to contract. Eventually, the waist regions' upper margins 13 will be formed with wrinkles or gathers. To overcome this problem, respective stretching ratios of the outer sheet 2 and the second elastic members 4 are preadjusted in the article 1 according to this invention by taking account of the residual strains peculiar to the outer sheet 2 and the second elastic members 4 so that the outer sheet 2 and the second elastic members 4 may have substantially the same dimensions in the transverse direction. In this way, there is no anxiety that any significant wrinkles or gathers might appear along the waist regions' upper margins 13 even after the outer sheet 2 and the second elastic members 4 have contracted.

Should the outer sheet 2 and the first and second elastic members 3, 4 exhibit substantially the same residual strains, the sheet 2 and these elastic members 3, 4 maybe joined together while these sheet 2 and elastic members 3, 4 are stretched at a same ratio. This is for the reason that, if these sheet 2 and elastic members 3, 4 are joined together while they are stretched at different ratios, respectively, a contractile force of the one would shorten the other, resulting in that the waist regions' upper margins 13 as well as the crotch region's lateral margins 15 would be formed with wrinkles or gathers.

It is possible to provide the front and rear waist regions 10, 12 of the outer sheet 2 with a plurality of auxiliary third elastic members extending in the transverse direction between the first elastic members 3 and the second elastic members 4. In this case, the stretching ratios at which the sheet 2 and the third elastic members are stretched in the transverse direction in the course of bonding these sheet 2 and third elastic members together may be appropriately preadjusted to ensure that these sheet 2 and third elastic members have substantially the same transverse dimensions after these sheet 2 and third elastic members have been relaxed.

Preferably, the outer sheet 2 exhibits a stretch stress of 0.05-0.5N/25 mm as the outer sheet 2 is stretched at a ratio of 10-20% and has a basis weight of 20-150 $g/m^2$. The elastically stretchable nonwoven fabric layers 8, 9 constituting are preferably stretchable by 100-400% in the longitudinal, transverse and waist-circumferential directions. These nonwoven fabric layers 8, 9 exhibit a same residual strain.

A stock material for the elastically stretchable nonwoven fabric layers 8, 9 may be selected from a series of products obtained by melt blown-, spun bond- and spun lace-processes. The component fibers may be, for example, elastically stretchable fibers obtained by a melt-spinning thermoplastic elastomer resin. It is desirable for the nonwoven fabric layers 8, 9 that respective test pieces (each having a diameter of 1 mm and a length of 3 mm) thereof exhibit a residual strain of 16% or less after these test pieces have been stretched by 50% (stretched twice at an ambient temperature of 20° C.). Now a stress exhibited by these test pieces (each having a diameter of 1 mm and a length of 100 mm) after these test pieces have been stretched by 50% (stretched once at a stretching rate of 100 mm/min at an ambient temperature of 40° C.) is represented by S1 while a stress exhibited by these test pieces (each having a diameter of 1 mm and a length of 100 mm) after these test pieces have been stretched by 50% (stretched once at an ambient temperature of 40° C.) and kept in such stretched state for 120 minutes is represented by S2. A stress retention represented by a ratio of S2/S1 is preferably 0.2 or higher. The nonwoven fabric layers 8, 9 having such physical properties advantageously have a high extensibility, a reliable resistance against deterioration of the stretch stress possibly occurring after these layers 8, 9 have been kept in the stretched state for a long period, and an adequate durability after repeated extension and contract twice or more often.

As the first and second elastic members 3, 4, natural or synthetic rubber in the form of threads or bands may be used. These elastic members 3, 4 preferably have an extensibility of 200-700%. It is also possible to use a foam rubber as a stock material for these elastic members 3, 4.

The outer sheet 2 may be formed also by a composite sheet consisting of an elastically stretchable hydrophobic fibrous nonwoven fabric layer and an elastically stretchable, breathable and liquid-impervious plastic film placed upon and joined to each other. The film preferably has the same physical properties as those of the above-described elastically stretchable nonwoven fabric layer. If the film has its physical properties different from those of the nonwoven fabric layer, stretching ratios of these film and nonwoven fabric layer at which they are joined to each other should be appropriately preadjusted by taking account of the respective residual strains peculiar to these film and nonwoven fabric layer so that these film and nonwoven fabric may have substantially same dimensions after they have been relaxed.

The outer sheet 2 may be formed also by a composite nonwoven fabric layer composed of an elastically stretchable hydrophobic fibrous nonwoven fabric layer made of a thermoplastic elastomer resin fibers and a hydrophobic fibrous nonwoven fabric layer made of crimped fibers obtained by a melt spinning thermoplastic synthetic resin such as polypropylene, polyethylene or polyester, the latter being placed on at least one surface of the former.

The panel 5 comprises a non-stretchable liquid-pervious topsheet 19 lying on a body facing side, a non-stretchable liquid-impervious backsheet 20 lying on an undergarment facing side and a liquid-absorbent core 21 interposed between these top- and backsheets 19, 20. The panel 5 has a substantially rectangular planar shape and extends between the front and rear waist regions 10, 12. The panel 5 has longitudinally opposite margins 5a formed by portions of the top- and backsheets 19, 20 extending outward beyond longitudinally opposite ends 21a of the core 21 in the longitudinal direction and transversely opposite lateral margins 5b formed by portions of the top- and backsheets 19, 20 extending outward beyond transversely opposite side edges 21b of the core 21 in the transverse direction. The top- and backsheets 19, 20 are placed upon and respective inner surfaces bonded to each other along the longitudinally opposite margins 5a and the transversely opposite lateral margins 5b of the panel 5 by means of adhesive (not shown). The core 21 is joined to the respective inner surfaces of the top- and backsheets 19, 20 by means of adhesive (not shown).

The panel 5 is provided along its lateral margins 5b with extensible elastic members 22 extending in the longitudinal direction. These elastic members 22 are attached to the lateral margins 5b under stretching in the longitudinal direction at a given ratio and are contractile in the longitudinal direction. The elastic members 22 are interposed between the top- and backsheets 19, 20 and secured to the respective inner surfaces of these sheets 19, 20 by means of adhesive (not shown). The lateral margins 5b are formed with a plurality of irregular wrinkles or gathers due to contraction of the elastic members 22.

The panel 5 has its longitudinally opposite margins 5a attached to the outer sheet 2 and its middle zone 5c attached to the lower margins 16 of the respective outer sheet sections in the crotch region. The outer surface of the backsheet 20 constituting the panel 5 is joined to the outer surface of the nonwoven fabric layer 8 constituting the outer sheet 2 by means of adhesive 23. Except the longitudinally opposite margins 5a and the middle zone 5c, the panel 5 is not joined to the outer sheet 2 and free with respect thereto. Preferably, the longitudinally opposite margins 5a are partially joined to the sheet 2.

To obtain a pants-configuration from the planar state shown by FIG. 1, the crotch region 11 is folded with the panel 5 inside, then the outer sheet sections 2a, 2b in the respective waist regions are put flat together along the waist regions' lateral margins 14 and bonded together in the vicinity of the side edges 17 of these waist regions' lateral margins 14 by means of a plurality of welding lines 18 (See FIG. 1).

In the article 1, the outer sheet 2 is formed with none of wrinkles or gathers along the waist regions' upper margins 13 as well as along the crotch region's lateral margins 15. Thus both the waist regions' upper margins 13 and the crotch region's lateral margins 15 are substantially planar and gaps will not be formed between the wearer's body and the waist regions' upper margins 13 and/or the crotch region's lateral margins 15 as the article 1 is worn. In this way, there is no possibility that bodily discharges might leak along the waist regions' upper margins 13 and/or the crotch region's lateral margins 15. The waist regions' upper margins 13 and the crotch region's lateral margins 15 are free from wrinkles or gathers and therefore the article 1 will not give the wearer uncomfortable feeling as the article 1 is worn. Furthermore, the first elastic members 3 and the elastic members 22 extend so as to form rings as the article 1 is worn and thereby to bring the peripheries of the leg-openings in close contact with entire circumferences of the wearer's legs.

Figure 5:
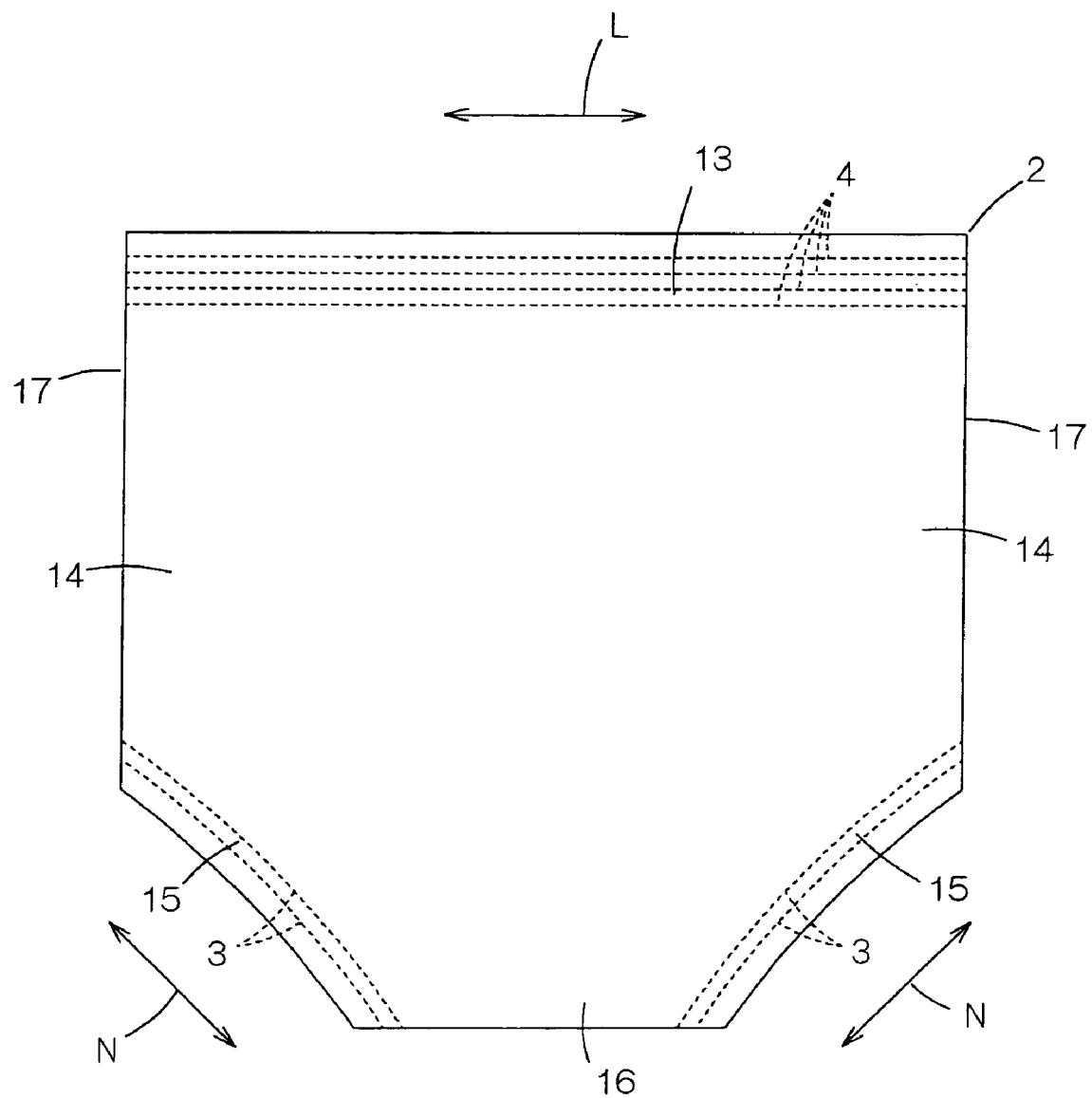
FIG. 5 is a plan view of an outer sheet.

FIG. 5 is a plan view of the outer sheet 2. In the outer sheet 2, a stretch stress in the second elastic members 4 is higher than that in the first elastic members 3. In the outer sheet 2, a transverse stretch stress in the waist regions' upper margins 13 is higher than a leg-circumferential stretch stress in the crotch region's lateral margins 15 as well as than a transverse stretch stress in the portion of the sheet 2 except the waist regions' upper margins 13 and the crotch region's lateral margins 15. In addition, a leg-circumferential stretch stress in the crotch region's lateral margins 15 is also higher than the transverse stretch stress in the portion of the sheet 2 except the waist regions' upper margins 13 and the crotch region's lateral margins 15. It is preferable for the outer sheet 2 that the transverse stretch stress in the waist regions' upper margins 13 is in a range of 0.2-0.6N/25 mm, the leg-circumferential stretch stress in the crotch region's lateral margins 15 is in a range of 0.1-0.4N/25 mm and the transverse stretch stress in the above-described portion 24 is in a range of 0.08-0.35N/25 mm. These values of stretch stress correspond to those obtained as the outer sheet 2 is stretched together with the elastic members 3, 4 by 110-120%.

If the stretch stress in the waist regions' upper margins 13 of the outer sheet 2 is less than that in the crotch region's lateral margins 15, specifically less than 0.2N/25 mm, movement of the wearer's legs is transmitted to the crotch region's lateral margins 15 so as to shift these crotch region's lateral margins 15 which, in turn, shift the waist regions' upper margins 13. Consequently, the article 1 is apt to slip down along the wearer's waist. On the contrary, if the stretch stress in the waist regions' upper margins 13 exceeds 0.6N/25 mm and the stretch stress in the portion 24 exceeds 0.35N/25 mm, the waist regions' upper margins 13 and the portion 24 will endurably tighten the wearer's waist and give the wearer uncomfortable feeling.

If the stretch stress in the crotch region's lateral margins 15 is less than 0.1N/25 mm, these crotch region's lateral margins can not adequately fit around the wearer's legs and it is apprehended that body discharges might leak out from these crotch region's lateral margins 15. If the stretch stress in the crotch region's lateral margins 15 exceeds 0.4N/25 mm, these crotch region's lateral margins will excessively tighten the wearer's legs and movement of the legs will be restrained by these crotch region's lateral margins 15.

Figure 6:
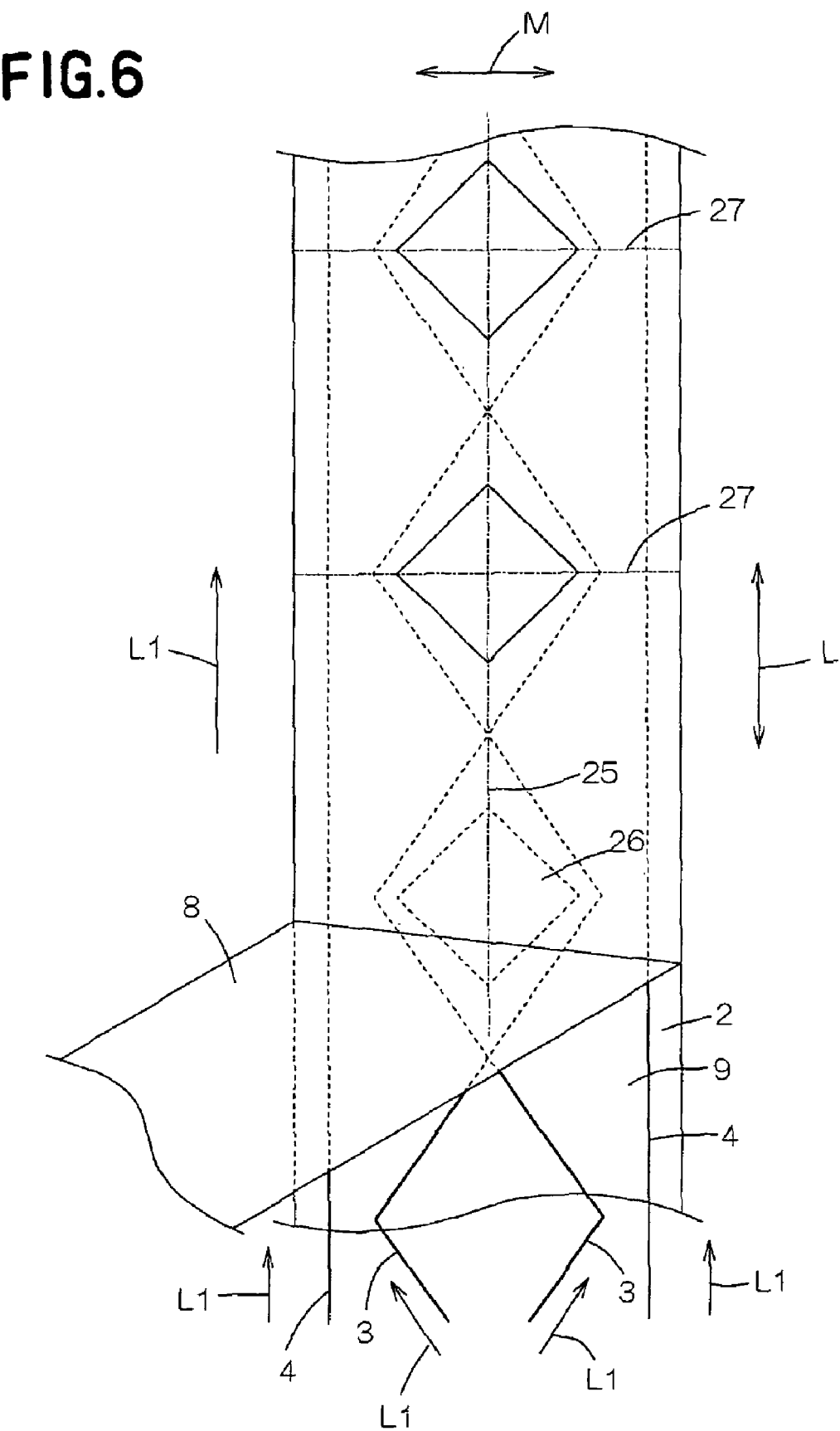
FIG. 6 is a diagram schematically illustrating an example of a production line for the outer sheet.
Figure 7:
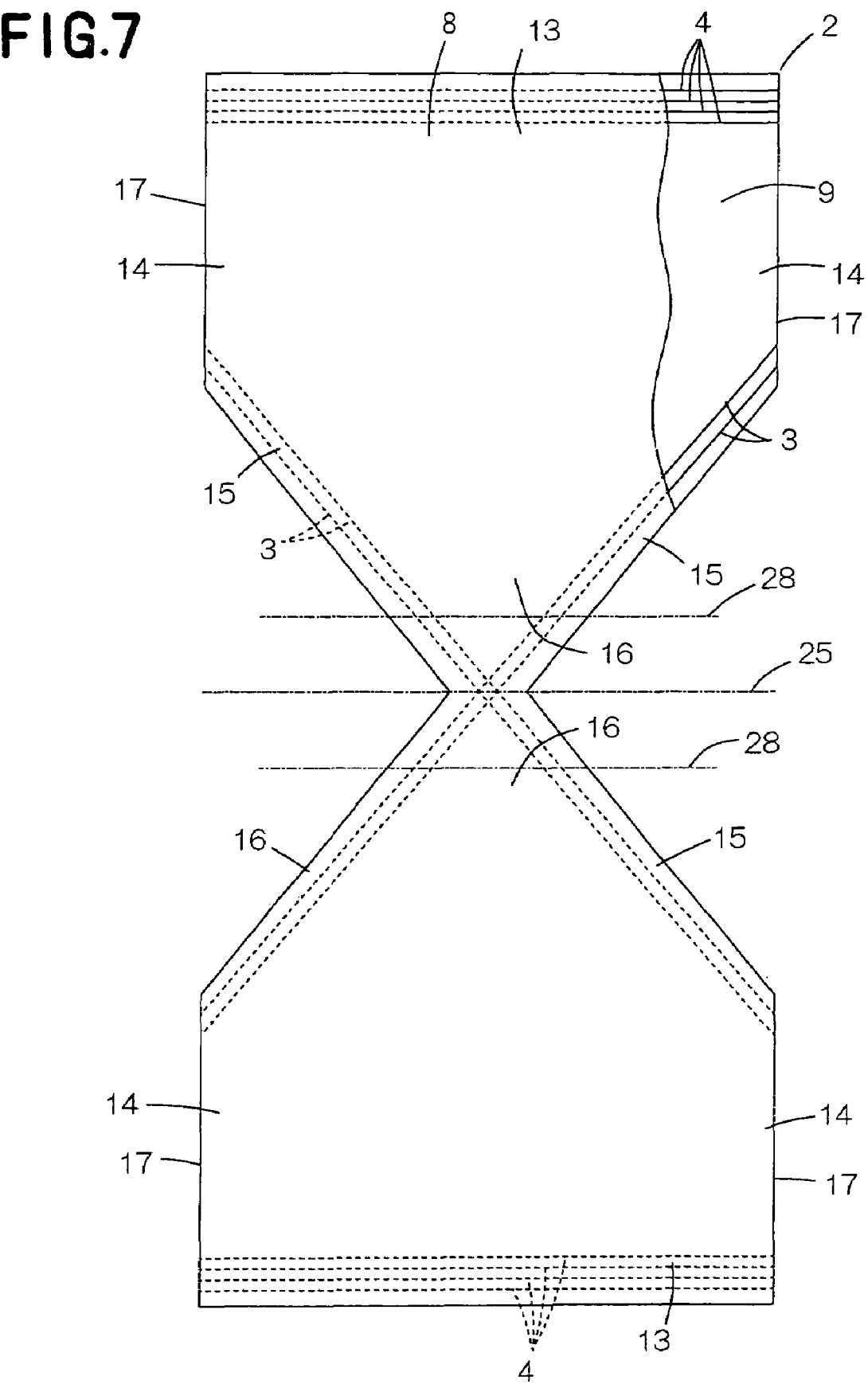
FIG. 7 is a plan view depicting the inner sheet as before the inner sheet is divided in two.
Figure 8:
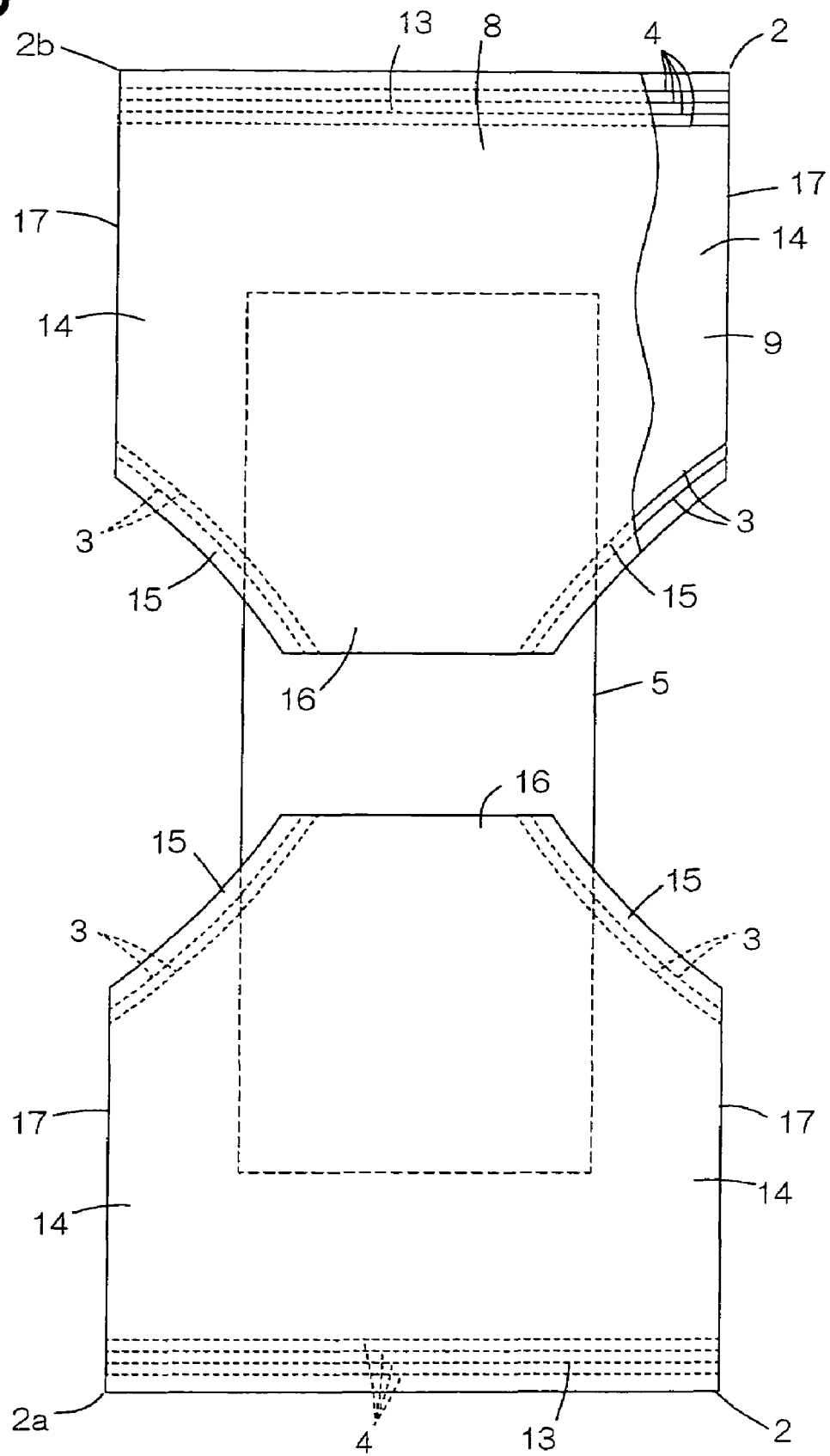
FIG. 8 is a diagram schematically illustrating a manner in which a panel is attached to the outer sheet.

FIG. 6 is a diagram schematically illustrating an example of a production line for the outer sheet 2, FIG. 7 is a plan view of the sheet 2 before it is bisected and FIG. 8 is a diagram illustrating a manner in which the panel 5 is attached to the outer sheet 2. In FIG. 6, a longitudinal direction is indicated by an arrow L and a transverse direction is indicated by an arrow M.

On the production line, the nonwoven fabric layers 8, 9 as well as the first and second elastic members 3, 4 are continuously running in the longitudinal direction indicated by an arrow L1 under a predetermined tension in the longitudinal direction thereof. On this production line, the first elastic members 3 extend at an angle of approximately 30-40° with respect to a longitudinal center line 25 of the outer sheet 2. Two groups of the first elastic members 3 repeat separation and intersection in the transverse direction of the outer sheet 2 so as to describe zigzag lines in the longitudinal direction of the sheet 2. The second elastic members 4 extend in parallel to the longitudinal center line 25 and describe substantially straight lines.

On the production line, the stretching ratios at which the elastic members 3, 4 and the nonwoven fabric layers 8, 9 (i.e., the outer sheet) are stretched are preadjusted to ensure that these elastic members 3,4 and nonwoven fabric layers 8, 9 may exhibit substantially same residual strains. The elastic members 3, 4 are interposed between these nonwoven fabric layers 8, 9 and secured to respective surfaces of these nonwoven fabric layers 8, 9 opposed to each other. Though not shown, adhesive is intermittently applied on at least one of these opposed surfaces of the nonwoven fabric layers 8, 9.

After the elastic members 3, 4 have been secured to the outer sheet 2, regions 26 enclosed by the first elastic members are cut out from the sheet 2 and then the sheet 2 is cut together with the elastic members 3, 4 along first cutting lines 27 extending in the transverse direction to obtain the outer sheet 2 of FIG. 7.

The individual outer sheet 2 of FIG. 7 obtained in the previous step is then cut along second cutting lines 28 extending on both sides of the center line 25 and thereby a transversely middle zone is cut out so as to divide the individual outer sheet 2 into the first and second outer sheet sections 2a, 2b. After divided, the first and second sheet sections 2a, 2b are spaced from each other by a given dimension in the transverse direction and the panel 5 is joined to the inner surfaces of these sheet sections 2a, 2b. The dimension by which these sheet sections 2a, 2b are spaced from each other in the crotch region 11 is preferably in a range of 4-6 cm.

A stock material for the topsheet 19 may be selected from a group consisting of a hydrophilic fibrous nonwoven fabric layer, a hydrophobic fibrous nonwoven fabric layer having a plurality of perforations and a plastic film having a plurality of fine perforations. A stock material for the backsheet 20 may be selected from a group consisting of a hydrophobic fibrous nonwoven fabric layer, a breathable liquid-impervious plastic film, a composite nonwoven fabric layer comprising two hydrophobic fibrous nonwoven fabric layers laminated on each other and a composite sheet comprising a hydrophobic fibrous nonwoven fabric layer and a breathable liquid-impervious plastic film laminated on each other. It is also possible to form the backsheet 20 using a melt blown fibrous nonwoven fabric layer having a high water-resistance and a spun bond fibrous nonwoven fabric layer having a high strength and a high flexibility laminated on at least one surface of the former.

The nonwoven fabric forming the top- and backsheets 19, 20 may be selected from a group consisting of products obtained by spun lace- needle punch-, melt blown-, thermal bond-, spun bond- and chemical bond-processes. The component fibers of the nonwoven fabric may be selected from a group consisting of polyolefin-, polyester- and polyamide-based fibers, and core-and-sheath type or side-by-side type conjugated fibers of polyethylene/polypropylene or polyethylene/polyester.

The core 21 comprises a mixture of fluff pulp and superabsorbent polymer particles or a mixture of fluff pulp, superabsorbent polymer particles and thermoplastic synthetic resin fibers, in any case, compressed to a desired thickness. Preferably, the core 21 is entirely covered with a liquid-pervious sheet such as a tissue paper or a hydrophilic fibrous nonwoven fabric layer in order to prevent the core 21 from getting out of its initial shape and/or to prevent any quantity of the polymer particles from falling off from the core 21. The adhesive may be selected from a group consisting of hot melt adhesive, acryl-based adhesive and rubber-based adhesive.

Joining of the sheets 2, 19, 20 one to another, attaching the elastic members 3, 4 to the sheet 2 and fixation of the core 21 to the sheets 19, 20 may be carried out using welding technique such as heat-sealing and sonic sealing.

The pants-type disposable wearing article according to this invention is primarily characterized in that the elastically stretchable outer sheet and the first elastic members attached to the crotch region's lateral margins have substantially same leg-circumferential dimensions without formation of any wrinkles or gathers after these outer sheet and first elastic members are relaxed. In this way, there is no possibility that any gap might be formed between the wearer's skin and the crotch region's lateral margins and any quantity of bodily discharges might leak out beyond these crotch region's lateral margins. In this article, the crotch region's lateral margins are substantially planar and it is not apprehended that the wearer might experience any uncomfortable feeling. In this article, the outer sheet cooperates with the first elastic members to achieve good fitness around the wearer's legs so that the crotch region's lateral margins may come in close contact with the wearer's legs and reliably prevent any quantity of bodily discharges from leaking out beyond these crotch region's lateral margins.

Similarly, the second elastic members are attached to the waist regions' upper margins of the outer sheet so that the outer sheet and the second elastic members may have substantially same transverse dimensions without formation of a plurality of irregular wrinkles or gathers after these outer sheet and second elastic members are relaxed. In this way, there is no possibility that any gap might be formed between the wearer's skin and the waist regions' upper margins and any quantity of bodily discharges might leak out beyond these waist regions' upper margins. In this article, the waist regions' upper margins are substantially planar and it is not apprehended that the wearer might experience any uncomfortable feeling. In this article, the outer sheet cooperates with the second elastic members to achieve good fitness around the wearer's waist and thereby to prevent the article from slipping down along the wearer's waist.

What is claimed is:

1. A pants-type disposable wearing article comprising an elastically stretchable outer sheet defining front and rear waist regions opposed to each other and a crotch region extending between these waist regions, and a liquid-absorbent panel attached to an inner surface of said outer sheet and extending between said front and rear waist regions, said outer sheet having waist regions' upper margins extending in said front and rear waist regions in a transverse direction, waist-circumferential lateral margins extending in a longitudinal direction and crotch region's lateral margins extending in said crotch region in the leg-circumferential direction, said front and rear waist regions being connected along said waist-circumferential margins so as to define a waist-opening and a pair of leg-openings, and first elastic members extending in the leg-circumferential direction are attached to said crotch region's lateral margins of said outer sheet, said pants-type disposable wearing article further comprising:

said outer sheet and said first elastic members being joined together while said outer sheet being stretched at a given stretching ratio in the transverse direction and said first elastic members being stretched at a given stretching ratio in the leg-circumferential direction so as to ensure that said outer sheet and said first elastic members have substantially same dimensions as measured in the leg-circumferential direction after these outer sheet and first elastic members have been relaxed and that said crotch region's lateral margins are substantially planar without undulation in a thickness direction of said outer sheet;

wherein said outer sheet comprises zones which underlie and are coextensive with the first elastic members, said zones being wrinkle-free when said outer sheet and said first elastic members are all relaxed; and wherein a peripheral edge of each of said leg-openings comprises a wrinkle-free section defined by one of said zones, and a wrinkled section defined by an associated one of transversely opposite edges of the panel, said transversely opposite edges of the panel having further elastic members attached thereto.

2. The wearing article according to claim 1, wherein waist-circumferential second elastic members extending in the transverse direction are attached to the waist regions' upper margins of said outer sheet and said outer sheet and said second elastic members are joined together while said outer sheet is stretched at a given stretching ratio and said second elastic members are stretched at a stretching ratio both in the transverse direction so as to ensure that said outer sheet and said second elastic members have substantially the same dimensions as measured in the transverse direction after these outer sheet and second elastic members have been relaxed and that said waist regions' upper margins are substantially planar without undulation in a thickness direction of said outer sheet.

3. The wearing article according to claim 2, wherein a transverse stretch stress in the waist regions' upper margins of said outer sheet is higher than a leg-circumferential stretch stress in the crotch region's lateral margins of said outer sheet and also than a transverse stretch stress in a portion of said outer sheet except said waist regions' upper margins and said crotch regiont's lateral margins.

4. The wearing article according to claim 2, wherein said outer sheet is formed by a composite nonwoven fabric layer composed of two elastically stretchable hydrophobic fibrous nonwoven fabric layers placed upon each other, and said first and second elastic members form no part of and are interposed between said nonwoven fabric layers.

5. The wearing article according to claim 2, wherein said outer sheet is formed by a composite sheet composed of an elastically stretchable hydrophobic fibrous nonwoven fabric layer and a breathable liquid-impervious plastic film joined together, and said first and second elastic members form no part of and are interposed between said nonwoven fabric layer and said film.

6. The wearing article according to claim 2, wherein
said zones underlie and are coextensive with both the first and second elastic members; and
when said outer sheet and said first and second elastic members are all relaxed, the first and second elastic members have the same dimensions as the respective said zones which are thereby wrinkle-free.

7. The wearing article according to claim 1, wherein said panel comprises a liquid-pervious topsheet lying on a body facing side, a liquid-impervious backsheet lying on an undergarment facing side and a liquid-absorbent core interposed between said top-and backsheets.

8. A pants-type disposable wearing article, comprising:
elastically stretchable front and rear outer sheets each being contoured by an upper edge, a lower edge and transversely opposite lateral edges connecting the upper and lower edges, each of said transversely opposite lateral edges comprising an upper section adjacent to the upper edge and a lower section adjacent to the lower edge;
a liquid-absorbent panel having longitudinally opposite ends attached to said front and rear outer sheets, respectively, thereby connecting said front and rear outer sheets together;
the upper sections of the transversely opposite lateral edges of said front and rear outer sheets being bonded to each other to define a waist hole and a pair of leg holes;
the upper edges of said front and rear outer sheets together defining a peripheral edge of said waist hole;
the lower sections of the transversely opposite lateral edges of said front and rear outer sheets defining at least partially peripheral edges of said leg holes; and
first elastic members bonded to and along the lower sections of the transversely opposite lateral edges of said front and rear outer sheets to extend in circumferential directions of said leg holes;
wherein
the panel is directly attached to the outer sheets only at the longitudinally opposite ends of said panel and at the lower edges of said outer sheets;
said first elastic members and the lower sections are bonded to each other when said first elastic members and outer sheets are stretched; and
when said first elastic members and outer sheets are all relaxed, a dimension of each said first elastic member as measured in the circumferential direction of the respective leg holes is substantially same as that of the respective lower section which underlies and is coextensive with said first elastic member, and said lower sections are thereby wrinkle free.

9. The wearing article according to claim 8, further comprising second elastic members bonded to and along the upper edges of said front and rear outer sheets to extend in a circumferential direction of said waist hole;

wherein said second elastic members and the upper edges are bonded to each other when said second elastic members and outer sheets are stretched; and when said second elastic members and outer sheets are all relaxed, a dimension of each said second elastic member as measured in the circumferential direction of said waist hole is substantially same as that of the respective upper edge which underlies and is coextensive with said second elastic member, and said upper edges are thereby wrinkle free.

10. The wearing article according to claim 9, wherein each of said outer sheets has a transverse stretch stress along the upper edge higher than a leg circumferential stretch stress along the lower sections; and the transverse stretch stress of each of said outer sheets along the upper edge is higher than that in a zone located outside the upper edge and the lower sections.

11. The wearing article according to claim 9, wherein each of said outer sheets comprises a composite sheet composed of two elastically stretchable hydrophobic fibrous nonwoven fabric layers joined together, and said first and second elastic members form no part of and are interposed between said nonwoven fabric layers.

12. The wearing article according to claim 9, wherein each of said outer sheets comprises a composite sheet composed of an elastically stretchable hydrophobic fibrous nonwoven fabric layer and a breathable liquid-impervious plastic film joined together, and said first and second elastic members form no part of and are interposed between said nonwoven fabric layer and said film.

13. The wearing article according to claim 9, wherein each of said outer sheets is one of
  (a) a composite sheet composed of two elastically stretchable hydrophobic fibrous nonwoven fabric layers joined together, wherein said first and second elastic members form no part of and are interposed between said nonwoven fabric layers; and
  (b) a composite sheet composed of an elastically stretchable hydrophobic fibrous nonwoven fabric layer and a breathable liquid-impervious plastic film joined together, wherein said first and second elastic members form no part of and are interposed between said nonwoven fabric layer and said film.

14. The wearing article according to claim 13, wherein in each of said outer sheets
  (i) a transverse stretch stress along the upper edge, which is oriented in a transverse direction of the article, is higher than a leg circumferential stretch stress along the lower sections, which are oriented obliquely to the transverse direction;
  (ii) the transverse stretch stress along the upper edge is than that in a middle zone of the outer sheet that is located between the upper edge and the lower sections; and
  (iii) the leg circumferential stretch stress along the lower sections is higher than the transverse stretch stress in said middle zone of the outer sheet.

15. The wearing article according to claim 13, wherein the lower edges of the outer sheets are exposed on an external surface of the article in a crotch region of the article.

16. The wearing article according to claim 13, wherein the peripheral edge of each of said leg holes is
  partially wrinkle-free in a first section defined by the lower sections of the respective transversely opposite lateral edges the outer sheets, and
  partially wrinkled in a second section defined by an associated one of transversely opposite edges of the panel, said transversely opposite edges of the panel having third elastic members attached thereto.

* * * * *